(12) United States Patent
Pomper et al.

(10) Patent No.: US 8,691,186 B2
(45) Date of Patent: *Apr. 8, 2014

(54) IMAGING INFECTION WITH COMPOUNDS THAT BIND TO THYMIDINE KINASE

(75) Inventors: Martin G. Pomper, Baltimore, MD (US); Chetan Bettegowda, Charlotte, NC (US); Catherine Foss, Baltimore, MD (US); Shibin Zhou, Owings Mills, MD (US); Kenneth Kinzler, Baltimore, MD (US); Bert Vogelstein, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/596,632

(22) Filed: Aug. 28, 2012

(65) Prior Publication Data

US 2013/0064767 A1  Mar. 14, 2013

Related U.S. Application Data

(62) Division of application No. 11/629,607, filed as application No. PCT/US2005/021888 on Jun. 20, 2005, now Pat. No. 8,273,326.

(60) Provisional application No. 60/581,222, filed on Jun. 18, 2004.

(51) Int. Cl.
*A61K 51/00* (2006.01)
*A61K 49/04* (2006.01)

(52) U.S. Cl.
USPC ........... 424/1.89; 424/1.73; 424/9.1; 424/9.2; 424/9.4

(58) Field of Classification Search
USPC ......... 424/1.11, 1.89, 9.3–9.5; 514/44, 45, 49
See application file for complete search history.

(56) References Cited

U.S. PATENT DOCUMENTS

| | | | |
|---|---|---|---|
| 5,879,661 A | 3/1999 | Conti et al. | |
| 5,969,139 A | 10/1999 | Martin et al. | |
| 6,331,278 B1 | 12/2001 | Copelan | |
| 6,331,287 B1 * | 12/2001 | Conti et al. | 424/1.89 |
| 2002/0128553 A1 | 9/2002 | Mishani et al. | |

OTHER PUBLICATIONS

J. Tjuvajev et al Salmoonella-based tumor targeted cancer therapy: tumor amplified protein expression therapy (TAPET) for diagnostic imaging, J. Control Release 74, 313-315, 2001.*
Roland Haubner et al., In vivo imaging of herpes simplex virus type 1 thymidine kinase gene expression: early kinetics of radiolabelled FIAU, European Journal of Nuclear Medicine, 2000, 27, 283-291.*
Bennett J.J., et al. "Positron emission tomography imaging for herpes virus infection: Implications for oncolytic viral treatments of cancer." Nat Med. Jul. 2001;7(7):859-63.
Bozenna Golankiewicz et al., "Fluorescent Tricyclic Analogues of Acyclovir and Ganciclovir, A Structure-Antiviral Activity Study", J. Med. Chem., vol. 44, (2001), pp. 4284-4287.
Chetan Bettegowda et al., "Imaging bacterial infections with radiolabeled 1-2(2'-deoxy-2'-fluoro-B-D-arabinofuranosyl)-5-iodouracil", PNAS, vol. 2, No. 4, Jan. 25, 2005, pp. 1145-1150.
Dang L.H., et al. "Combination bacteriolytic therapy for the treatment of experimental tumors." Proc Natl Acad Sci U S A. Dec. 18, 2001;98(26):15155-60.
Saito Y et al., "Diagnostic imaging of herpes simplex virus encephalitis using a radiolabeled antiviral drugs : autoradiographic assessmjent in an animal model" Annals of Neurology vol. 15(6). Jun. 1984, pp. 548-558.
Saito H., et al. "Further studies on thymidine kinase: distribution pattern of the enzyme in bacteria." J Gen Microbiol. Nov. 1985;131(11):3091-8.
Saito H., et al. "Thymidine kinase of bacteria: activity of the enzyme in actinomycetes and related organisms." J Gen Microbiol. Jul. 1984;130(7):1863-70.
Saito et al. Diagnostic Imaging of Herpes Simplex Virus Encephaliitis Using a Radiolabeled Antiviral Drug: Autoradiographi Assessment in an animal moedl, Ann. Neurol 15, 548-558, 1984.
Tjuvajev et al. Salmoonella-based tumor targeted cancer therapy: tumor amplified protein expression therapy (TAPET) for diagnostic imaging, J. Control Release 74, 313-315, 2001.
Tomasz Goslinkski et al, "Synthesis and Biological Activity of Strongly Fluorescent Tricyclic Analogues of Acyclovir and Ganciclovir", J. Med. Chem., vol. 45, (2002), pp. 5052-5057.
Win-Ping Deng et al., "Non-invasive in vivo imaging with radiolabeled FIAU for monitoring cancer gene therapy using herpes simplex virus type 1 thymidien kinase and ganciclovir", European Journal of Nuclear Medicine and Molecular Imaging, vol. 31, No. 1, Jan. 2004, pp. 99-109.

* cited by examiner

*Primary Examiner* — Michael G Hartley
*Assistant Examiner* — Jagadishwar Samala
(74) *Attorney, Agent, or Firm* — Jeffrey W. Childers

(57) ABSTRACT

The instant invention provides a method for diagnosing an infection in a subject by administering to the subject a compound suitable for imaging which binds to a thymidine kinase present in the infecting organism, and obtaining an image of the subject to determine the presence and location of the compound, wherein a localization of the compound is indicative that the subject has an infection.

8 Claims, No Drawings

IMAGING INFECTION WITH COMPOUNDS THAT BIND TO THYMIDINE KINASE

RELATED APPLICATIONS

This application is a divisional of U.S. patent application Ser. No. 11/629,607 filed Jun. 16, 2008 which is a National Phase Application of PCT/US2005/21888 filed Jun. 20, 2005 which claims the benefit of U.S. Provisional Application No.: 60/581,222, filed Jun. 18, 2004, the entire contents of each are incorporated herein by reference in their entireties.

GOVERNMENT SPONSORED RESEARCH

The work was supported by in part, by NIH grants CA062924, CA43460, CA92871 and CA103175.

SEQUENCE LISTING

The instant application contains a Sequence Listing which has been submitted in ASCII format via EFS-Web and is hereby incorporated by reference in its entirety. Said ASCII copy, created on Nov. 13, 2012, is named 63546DIV.txt and is 1,394 bytes in size.

BACKGROUND OF THE INVENTION

The ability to diagnose and localize an infection in a subject are critical to the practicing clinician. Current methods to visualize bacterial infection in vivo use positron emission tomography with radiolabeled white blood cells or, more recently, radiolabeled antibiotics. These methods tend to be nonspecific and cannot distinguish infection from inflammation or cancer. For example, Sarda et al. tested $^{99m}$Te-labeled ciprofloxacin for imaging S. aureus infection in the knee joints of rabbits. Their results indicated that this compound lacks the specificity necessary for clinical applications ((2002) J. Nucl. Med 43:239-45). In another study, Fishman et al. determined that $^{18}$F-labeled fluconazole lacked the specificity to effectively visualize Candida in a rabbit model of infection ((1991) J. Pharmacol. Exp. Ther. 259:1351-9)

Accordingly, the need exists for an organism specific non-invasive imaging method to detect infection, e.g., bacterial, viral or fungal infection in a subject.

SUMMARY OF THE INVENTION

In one aspect, the instant invention provides a method for diagnosing an infection in a subject by administering to the subject a compound suitable for imaging which binds to a thymidine kinase present in the infecting organism, and obtaining an image of the subject to determine the presence and location of the compound, wherein a localization of the compound is indicative that the subject has an infection.

In a specific embodiment, the infection is a bacterial, viral or fungal infection. In a further specific embodiment, the infection is a bacterial infection and the thymidine kinase is a bacterial thymidine kinase.

In one embodiment, the image of the subject is acquired by a method selected from the group consisting of planar gamma imaging, single photon emission computed tomography (SPECT) and positron emission tomography (PET).

In another embodiment, the compound is a nucleoside analog. In a specific embodiment, the nucleoside analog is radiolabeled, e.g., with fluorine or iodine. In certain embodiments, the nucleoside analog emits gamma particles. Exemplary compounds used in the methods include, for example, 2'-fluoro-2'deoxy-1-beta-D-arabinofuranosyl-5-iodo-uracil ([125I]-FIAU), 2'-fluoro-2'deoxy-1-beta-D-arabinofuranosyl-5-iodo-uracil ([124I]-FIAU), 9-(4-18F-fluoro-3-[hydroxymethyl]butyl)guanine ([18F]-FHBG), (18)F-1-(2'-deoxy-2'-fluoro-beta-d-arabinofuranosyl)thymine ([18F]-FMAU), 18F-2'-fluoro-2'deoxy-1beta-D-arabinofuranosyl-5-ethyl-uracil ([18F]-FEAU) and 1-(2'-deoxy-2'-fluoro-beta-D-arabinofuranosyl)-5-[18F]iodouracil ([18F]-FIAU).

In a related embodiment, the nucleoside analog is fluorescent.

In certain embodiments, the bacterial infection is caused by bacteria from a genus selected from the group consisting of *Escherichia*, *Bacillus*, *Chromobacterium*, *Clostridium*, *Enteroccus*, *Haemophilus*, *Listeria*, *Mycoplasma*, *Pasteruella*, *Salmonella*, *Staphylococcus*, *Streptococcus*, *Streptomyces*, *Vibrio*, and *Yersinia*.

In another aspect, the invention provides a method for imaging a bacterial infection in a subject by administering to the subject a compound suitable for imaging which binds to a bacterial thymidine kinase, and obtaining an image of the subject; thereby obtaining an image of a bacterial infection in a subject.

In a related embodiment, the image of the subject is acquired by a method selected from the group consisting of planar gamma imaging, single photon emission computed tomography (SPECT) and positron emission tomography (PET).

In another embodiment, the compound is a nucleoside analog. In a specific embodiment, the nucleoside analog is radiolabeled, e.g., with fluorine or iodine. In certain embodiments, the nucleoside analog emits gamma particles. Exemplary compounds used in the methods include, for example, 2'-fluoro-2'deoxy-1-beta-D-arabinofuranosyl-5-iodo-uracil ([125I]-FIAU), 2'-fluoro-2'deoxy-1-beta-D-arabinofuranosyl-5-iodo-uracil ([124I]-FIAU), 9-(4-18F-fluoro-3-[hydroxymethyl]butyl)guanine ([18F]-FHBG), (18)F-1-(2'-deoxy-2'-fluoro-beta-d-arabinofuranosyl)thymine ([18]-FMAU), 18F-2'-fluoro-2'deoxy-1beta-D-arabinofuranosyl-5-ethyl-uracil([18F]-FEAU) and 1-(2'-deoxy-2'-fluoro-beta-D-arabinofuranosyl)-5-[18F]iodouracil ([18F]-FIAU).

In a related embodiment, the nucleoside analog is fluorescent.

In another related embodiment, the compound suitable for imaging is an antimicrobial compound. For example, the compound, in addition to being suitable for imaging, can be an antibiotic, antiviral, or antifungal compound.

In another related embodiment, the invention allows for the differentiation of bacterial infection and inflammation or cancer.

In another aspect, the invention provides method for monitoring the efficacy of treatment in a subject having an infection by administering to the subject a first dose of a compound suitable for imaging which binds to a thymidine kinase present in the infecting organism, obtaining a first image of the subject to determine the presence and location of the compound, administering to the subject a second dose of a compound suitable for imaging which binds to a thymidine kinase present in the infecting organism at a time subsequent to the first administration, and obtaining a second image of the subject to determine the presence and location of the compound, wherein a decrease in the amount of compound localized in the image is indicative of effective therapy.

In certain embodiments the infection is a bacterial, viral or fungal infection. In a specific embodiment, the infection is a bacterial infection and the thymidine kinase is a bacterial thymidine kinase.

In one embodiment, the image of the subject is acquired by a method selected from the group consisting of planar gamma imaging, single photon emission computed tomography (SPECT) and positron emission tomography (PET).

In another embodiment, the compound is a nucleoside analog. In a specific embodiment, the nucleoside analog is radiolabeled, e.g., with fluorine or iodine. In certain embodiments, the nucleoside analog emits gamma particles. Exemplary compounds used in the methods include, for example, 2'-fluoro-2'deoxy-1-beta-D-arabinofuranosyl-5-iodo-uracil ([125I]-FIAU), 2'-fluoro-2'deoxy-1-beta-D-arabinofuranosyl-5-iodo-uracil ([124I]-FIAU), 9-(4-18F-fluoro-3-[hydroxymethyl]butyl)guanine ([18F]-FHBG), (18)F-1-(2'-deoxy-2'-fluoro-beta-d-arabinofuranosyl)thymine ([18F]-FMAU), 18F-2'-fluoro-2'deoxy-1beta-D-arabinofuranosyl-5-ethyl-uracil ([18F]-FEAU) and 1-(2'-deoxy-2'-fluoro-beta-D-arabinofuranosyl)-5-[18F]iodouracil ([18F]-FIAU).

In a related embodiment, the nucleoside analog is fluorescent.

In certain embodiments, the bacterial infection is caused by bacteria from a genus selected from the group consisting of *Escherichia, Bacillus, Chromobacterium, Clostridium, Enteroccus, Haemophilus, Listeria, Mycoplasma, Pasteruella, Salmonella, Staphylococcus, Streptococcus, Streptomyces, Vibrio*, and *Yersinia*.

In another related embodiment, the compound suitable for imaging is an antimicrobial compound. For example, the compound, in addition to being suitable for imaging, can be an antibiotic, antiviral, or antifungal compound.

In another aspect, the invention provides a method for imaging bacterial-based anticancer therapy by administering to a subject a compound suitable for imaging which binds to a thymidine kinase present in the therapeutic bacteria, and imaging the subject to determine the presence and location of the compound, thereby imaging a bacterial-based anticancer therapy.

In one embodiment, the image of the subject is acquired by a method selected from the group consisting of planar gamma imaging, single photon emission computed tomography (SPECT) and positron emission tomography (PET).

In another embodiment, the compound is a nucleoside analog. In a specific embodiment, the nucleoside analog is radiolabeled, e.g., with fluorine or iodine. In certain embodiments, the nucleoside analog emits gamma particles. Exemplary compounds used in the methods include, for example, 2'-fluoro-2'deoxy-1-beta-D-arabinofuranosyl-5-iodo-uracil ([125I]-FIAU), 2'-fluoro-2'deoxy-1-beta-D-arabinofuranosyl-5-iodo-uracil ([124I]-FIAU), 9-(4-18F-fluoro-3-[hydroxymethyl]butyl)guanine ([18F]-FHBG), (18)F-1-(2'-deoxy-2'-fluoro-beta-d-arabinofuranosyl)thymine ([18F]-FMAU), 18F-2'-fluoro-2'deoxy-1beta-D-arabinofuranosyl-5-ethyl-uracil ([18F]-FEAU) and 1-(2'-deoxy-2'-fluoro-beta-D-arabinofuranosyl)-5-[18F]iodouracil ([18F]-FIAU).

In a related embodiment, the nucleoside analog is fluorescent.

DETAILED DESCRIPTION OF THE INVENTION

The present invention is based, at least in part, on the discovery using suitably functionalized compounds that binds to a polypeptide, e.g., a thymidine kinase, expressed by an infectious organism allows for imaging of the infection. This invention is directed, at least in part, to the diagnosis and localization of infection, e.g., infections caused by bacteria, virus, or fungi. This present invention allows, for example, for the visualization of infectious foci, localization of tumors harboring anaerobic bacteria, diagnosis of infection, monitoring antibacterial therapy, studying of bacterial trafficking for emerging bacterial-based therapies of cancer and for treatment of infection by noninvasive means.

The term "treated," "treating" or "treatment" includes the diminishment or alleviation of at least one symptom associated or caused by the state, disorder or disease being treated. In certain embodiments, the treatment comprises the induction of a Pin1 inhibited state, followed by the activation of the Pin1 modulating compound, which would in turn diminish or alleviate at least one symptom associated or caused by the Pin1 associated state, disorder or disease being treated. For example, treatment can be diminishment of one or several symptoms of a disorder or complete eradication of a disorder.

The term "subject" is intended to include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from an infection or cancer.

The term "cancer" includes malignancies characterized by deregulated or uncontrolled cell growth, for instance carcinomas, sarcomas, leukemias, and lymphomas. The term "cancer" includes primary malignant tumors, e.g., those whose cells have not migrated to sites in the subject's body other than the site of the original tumor, and secondary malignant tumors, e.g., those arising from metastasis, the migration of tumor cells to secondary sites that are different from the site of the original tumor.

The language "effective amount" of a compound is the amount necessary or sufficient to provide a readable signal when imaged using the techniques described herein, e.g., planar gamma imaging, single photon emission computed tomography (SPECT) and positron emission tomography (PET). The effective amount can vary depending on such factors as the size and weight of the subject, the type of illness, or the particular compound. For example, the choice of the compound can affect what constitutes an "effective amount". One of ordinary skill in the art would be able to study the factors contained herein and make the determination regarding the effective amount of the compound without undue experimentation.

The term "compound" is intended to include compounds that are capable of being imaged by, for example, by planar gamma imaging, single photon emission computed tomography (SPECT) or positron emission tomography (PET). The compounds may be radiolabeled or fluorescent. In specific embodiments, the compounds are nucleosides or nucleoside analogs that bind to a kinase, e.g., a thymidine kinase.

The phrase "pharmaceutically acceptable carrier" is art recognized and includes a pharmaceutically acceptable material, composition or vehicle, suitable for administering compounds used in the methods described herein to subjects, e.g., mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

As used herein, the term "imaging" refers to the use of any imaging technology to visualize a detectable compound after administration to a subject, by measuring the energy emitted by the compound after localization of the compound following administration. Imaging technologies such as positron emission tomography (PET) and the like are applied.

As used herein, "positron emission tomography imaging" or "PET" incorporates all positron emission tomography imaging systems or equivalents and all devices capable of positron emission tomography imaging. The methods of the invention can be practiced using any such device, or variation of a PET device or equivalent, or in conjunction with any known PET methodology. See, e.g., U.S. Pat. Nos. 6,151,377; 6,072,177; 5,900,636; 5,608,221; 5,532,489; 5,272,343; 5,103,098, each of which is incorporated herein by reference. Animal imaging modalities are included, e.g., micro-PETs (Corcorde Microsystems, Inc.).

Compounds of the Invention

The methods described herein make use of compounds that bind to kinase polypeptides, e.g., a thymidine kinase polypeptides, in an organism and produce a detectable signal that can used to obtain an image of a subject and, thereby, determine the presence and location of the organism. The compounds used in the methods of the invention bind to a kinase within the organism, e.g., a thymidine kinase, with greater affinity than they bind to a kinase, e.g., a thymidine kinase, in the subject to which they are administered. Thymidine kinases are particularly well suited for the methods of the invention. The bacterial thymidine kinases have a consensus sequence in the kinase catalytic domain that is not present in the kinase catalytic domain of mammalian thymidine kinases (see the Examples). Accordingly, compounds with high affinity for bacterial thymidine kinases exhibit greatly reduced affinity for mammalian thymidine kinases.

The invention utilizes compounds that are easily synthesized and are detectable to an imaging apparatus, e.g., a PET or SPECT instrument. In one embodiment, the compounds are nucleoside analogs that bind to a kinase. In a specific embodiment, the kinase is a thymidine kinase. Bioinformatic analysis of the 53 pathogenic bacteria whose genomes have been sequenced reveled that every species has a thymidine kinase (Bettegowda et al. (2005) *PNAS* 102:1145-50).

In specific embodiments the nucleoside analogs are labeled with a radioisotope, e.g., a radioisotope of iodine or fluorine. In another embodiment, the nucleoside analogs may be fluorescent.

Preferred radiolabeled compounds of the invention are nucleoside analogs that are easily synthesized and limited in vivo catabolism. Compounds such as those described in U.S. Pat. Nos. 5,879,661 and 6,331,287 can be used with the methods of the invention. Other exemplary compounds useful in the methods of the invention include, for example, 2'-fluoro-2'deoxy-1-beta-D-arabinofuranosyl-5-iodo-uracil ([125I]-FIAU), 2'-fluoro-2'deoxy-1-beta-D-arabinofuranosyl-5-iodo-uracil ([124I]-FIAU), 9-(4-18F-fluoro-3-[hydroxymethyl]butyl)guanine ([18F]-FHBG), (18)F-1-(2'-deoxy-2'-fluoro-beta-d-arabinofuranosyl)thymine ([18F]-FMAU), 18F-2'-fluoro-2'deoxy-1beta-D-arabinofuranosyl-5-ethyl-uracil ([18F]-FEAU) and 1-(2'-deoxy-2'-fluoro-beta-D-arabinofuranosyl)-5-[18F]iodouracil ([18F]-FIAU).

Exemplary fluorescent compounds that may be used in the methods of the invention have recently been described by Golankiewicz et al. ((2001) *J. Med. Chem.*

44:4284-7) and Goslinski et al. ((2002) *J. Med. Chem.* 45:5052-7). The fluorescent tricyclic acyclovir and ganciclovir analogs described by Goslinski et al., particularly GCV3, are contemplated for use in the claimed methods.

Imaging

Generally, imaging techniques involve administering a compound to a subject that can be detected externally to the subject. Images are generated by virtue of differences in the spatial distribution of the imaging agents which accumulate in various locations in a subject. The methods of the present invention, the imaging techniques rely on the compounds being preferentially bound by the organism, e.g., the infectious organism. The spatial distribution of the imaging agent accumulated in a subject, e.g., in an infected region, may be measured using any suitable means, for example, planar gamma imaging, single photon emission computed tomography (SPECT) and positron emission tomography (PET). Alternatively, imaging techniques that detect fluorescence may be used in the methods of the invention.

Among the most commonly used positron-emitting nuclides in PET are $^{11}C$, $^{13}N$, $^{15}O$, and $^{18}F$. Isotopes that decay by electron capture and/or γ emission are used in SPECT, and include, for example, $^{123}I$ and $^{124}I$.

Particularly preferred in the methods of the invention is PET. Specifically, imaging is carried out by scanning the entire patient, or a particular region of the patient using the detection system, and detecting the signal, e.g., the radioisotope signal. The detected signal is then converted into an image. The resultant images should be read by an experienced observer, such as, for example, a physician. The foregoing process is referred to herein as "imaging" the patient. Generally, imaging is carried out about 1 minute to about 48 hours following administration of the compound used in the methods of the invention. The precise timing of the imaging will be dependant upon such factors as the clearance rate of the compound administered, as will be readily apparent to those skilled in the art. Preferably, imaging is carried out between about 1 minute and about 4 hours following administration.

Once an image has been obtained, one of skill in the art will be able to determine the location of the compound. Using this information, the artisan can determine, for example, if an infection is present, the extent of the infection, or the efficacy of treatment which the subject is undergoing. Images obtained at different time points, e.g., 12, 24, 36, 48 or more, hours apart are particularly useful in determining the efficacy of treatment, e.g., antiviral, antibacterial, or antifungal treatment.

Unlike methods currently used, the imaging methods described herein allow the clinician to distinguish infection from inflammation and cancer.

Dosage and Formulation

The compounds used in the methods of the present invention can be administered orally using any pharmaceutically acceptable dosage form known in the art for such administration. The compound can be supplied in solid dosage forms such as dry powders, granules, tablets or capsules, or in liquid dosage forms, such as syrups or aqueous suspensions. The compound can be administered alone, but is generally administered with a pharmaceutical carrier. A valuable treatise with respect to dosage forms is Remington's Pharmaceutical Sciences, Mack Publishing.

The compounds used in the methods of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the art.

The compounds used in the methods of the invention can be administered by any means that produces contact of the compound with the compound's site of action in the body of a host, such as a human or a mammal. They can be administered alone or with a pharmaceutical carrier selected on the basis of the chosen route of administration and standard pharmaceutical practice.

The dosage regimen for the compounds determined from the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine an effective amount of the compound to administer to a subject.

The compounds used in the methods of the present invention can be administered in intranasal form via topical use of suitable intranasal vehicles, or via transdermal routes, using those forms of transdermal skin patches wall known to those of ordinary skill in that art.

In the methods of the present invention, the compounds described herein can be administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or .beta.-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the methods of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds used in the methods of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds determined from the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

This invention is further illustrated by the following examples, which should not be construed as limiting.

EXAMPLES

Materials and Methods

In Vitro Bacterial Susceptibility Assays 1-(2'-deoxy-2'-fluoro-β-D-arabinofuranosyl)-5-iodouracil (FIAU) (Moravek catalog no. M251) and penciclovir (Moravek catalog no. M972) were purchased from Moravek Biochemicals (Brea, Calif.). Zidovudine was purchased from Glaxo Wellcome. Bacterial susceptibility tests were performed in 96-well microtiter plates (VWR Scientific), with serial dilutions of drug placed in each well. Each well was inoculated with *Escherichia coli* (Yale University *E. coli* Genetic Stock Center, New Haven, Conn.) and grown in Luria broth (Invitrogen) at 37° C. *E. coli* TK mutants were generated by selecting for spontaneously resistant colonies on plates containing 1 mg/ml Zidovudine. Ten resistant clones were selected and screened for deletions in the TK gene by using the PCR primers SZ46-eTKKO20F and (5'-TGAT-GAAAAGTAGAACAGTCG-3' (SEQ ID NO: 1)) SZ49-eTK-K0789R (5'-ATCAAGACGCAGCACCATG-3' (SEQ ID NO: 2)). One resistant clone was found to contain a deletion in the TK gene and was used for subsequent experiments.

As a control for integrity of the DNA of this clone, its 16S rRNA gene was amplified by using the primers SZ-16S-Ecoli993F (5'-ACATCCACGGAAGTTT-TCAG-3' (SEQ ID NO: 3)) SZ 16S-Ecoli454R (5'-CCGAAGGTTAAGC-TAC-CTAC-3' (SEQ ID NO: 4)).

Tumor Inoculation and Spore Administration

All animal experiments were overseen and approved by the Animal Welfare Committee of The John Hopkins University and were in compliance with university standards. Six- to 8-wk-old athymic nu/nu or BALB/c mice, purchased from Harlan Bioproducts for Science (Indianapolis), were used for tumor implantation studies. Five million cells were injected s.c. into the right flank of each mouse. Tumor volume was calculated as length×width$^2$×0.5, and mice were treated with *Clostridium novyi*-NT spores when tumors occupied ~250 mm$^3$. *C. novyi*-NT spores were prepared as described (15), and mice were i.v. injected with 300 million spores suspended in 250 µl of PBS.

TABLE 1

Bacterial strains imaged after i.m. injection

| Organism | Clinical significance |
|---|---|
| *E. coli* | Adult and infantile diarrhea, urinary tract infection, pneumonia, meningitis, and abscess |
| *E. faecalis* 49532 | Nosocomial infection including vancomycin-resistant enterococci, urinary tract infection, endocarditis, abscess, and meningitis |
| *S. pneumoniae* 49619 | Pneumonia, meningitis, sinusitis, osteomyelitis, and sepsis |
| *S. aureus* 29213 and 25293 | Cellulitis, indwelling medical device infection, diabetic ulcer, postsurgical wounds, osteomyelitis, endocarditis, meningitis, mastitis, phlebitis, pneumonia, boils, furuncles, and impetigo |
| *S. epidermidis* F362 | Endocarditis, cellulitis, urinary tract infection, and indwelling medical device infection |

[$^{125}$I]FIAU Preparation

Briefly, 1-(2'-deoxy-2'-fluoro-β-D-arabinofuranoside)-uracil (300 µg, 1.22 mmol, Moravek) was dissolved in 170 µl of 2 M HNO$_3$. To this solution, 1.5 mCi (1 Ci=37 GBq) of [I-$^{125}$] NaI.(ICN) was added and the contents heated at 130° C. for 45 min. The reaction was quenched with 150 µl of HPLC mobile phase (20:79.9:0.1% MeCN:H$_2$O:triethylamine). The resulting [$^{125}$I]FIAU was purified by reverse-phase HPLC by using two passages over a Phenomenex Luna C$_{18}$ semiprep column (10 µm, 4.6×250 mm, Phenomenex, Torrance, Calif.) by using the above-mentioned isocratic mobile phase at a flow rate of 2 ml/min. The product was concentrated under reduced pressure and formulated in 0.9% physiological saline before sterile filtration through a 0.22-µm syringe filter. Formulations were kept at 1 mCi/ml to minimize the injection volume. The final radiochemical yield was 50%, the radiochemical purity was >99%, and the specific radioactivity was >2,000 Ci/mmol.

Experimental Infections

*E. coli* strains or clinical isolates from the Johns Hopkins Hospital Microbiology Laboratory, including *Staphylococcus aureus* 29213 and 25923, *Streptococcus pneumoniae* 49619, *Enterococcus faecalis* 49532, and *Staphylococcus epidermidis* F362, were used to create experimental infections. Bacteria were grown to log phase in Mueller Hinton Broth with Cations (Remel, Lenexa, Kans.) or BBL Todd Hewitt Broth (Becton Dickinson). Localized infections were generated by injecting 1×10$^9$ *E. coli* and ≈1×10$^8$ of the other bacterial strains into mouse thighs. Morphologic examinations of the infectious lesions in the thighs of mice injected with the TK-deficient (TK−) strain of *E. coli* showed that they were as intense as those resulting from WT *E. coli*. To quantify the minimal number of bacteria required to generate signals upon imaging, mice were injected in the thigh with various amounts of *S. aureus* 25923. One hour later, the mice were killed, the muscles were harvested and homogenized, and the extracts spread on blood agar plates (Becton Dickinson) for colony counting. The plating efficiency of *S. aureus* 25923 grown in liquid media was found to be >95%.

In Vivo Imaging

Mice were injected with 225 µCi of [$^{125}$I]FIAU via the tail vein and imaged at various time points thereafter. Before imaging, mice were anesthetized via s.c. administration of acepromazine and ketamine. Each scan took min with a dedicated small-animal single-photon emission computed tomography (SPECT)/computed tomography (CT) camera (Gamma Medica X-SPECT, Northridge, Calif.) in planar acquisition mode using a low-energy high-resolution (LEHR) parallel-hole collimator. For each bacterial strain used, at least two mice were injected and imaged. To obtain SPECT/CT images, animals were first scanned for ≈40 min by using a small-animal SPECT camera in tomographic acquisition mode, using two LEHR parallel-hole collimators. The animals then underwent CT by using appropriate fiducial markers that allowed coregistration.

Biodistribution

Imaging experiments showed that high signal-to-noise ratios in infectious foci could be consistently obtained 24 h after [$^{125}$I]FIAU administration. Accordingly, this time point was chosen for detailed analyses. Biodistribution studies were performed in mice injected with 1×10$^8$ *S. aureus* 25923 into one thigh. Six hours later, the mice were injected with 2 µCi of [$^{125}$I]FIAU, and, after another 24 h, the mice were killed, their organs were harvested, and radioactivity was determined.

Susceptibility of *E. coli* to Nucleoside Analogs

To determine whether endogenous bacterial TK could provide a reporter enzyme suitable for imaging, the susceptibility of *E. coli* to a variety of common nucleoside analogs was examined in vitro. Growth inhibition indicated that the nucleoside analog was a substrate for the *E. coli* TK and could thereby serve as an imaging reporter when radiolabeled. *E. coli* proved resistant to genciclovir and penciclovir but quite sensitive to FIAU and Zidovudine.

To determine whether the TK gene was responsible for this sensitivity, a derivative of *E. coli* in which the TK gene was deleted was created. PCR was used to demonstrate the absence of the TK gene in this derivative. The TK strain was moderately resistant to Zidovudine and highly resistant to FIAU. Because FIAU can be radiolabeled by using commercially available reagents and has been successfully used to image tumor cells transfected with HSV1-TK, it was elected to test its potential for imaging bacterial infections.

In Vivo Imaging of *E. coli* Infections

[$^{125}$I]FIAU was synthesized by standard methods and injected i.v. into animals 6 h after intramuscular inoculations of bacteria into the thighs of mice. Whole-body planar scintigram demonstrated the uptake of [$^{125}$I]FIAU within the thighs of mice harboring WT *E. coli* bacteria. Signals from the infectious lesions could be seen as early as 2 h after injection of [$^{125}$I]FIAU and were optimal 16 h after injection. Infections of the same mice inoculated with TK-*E. coil* in the opposite thighs showed no discernable uptake of [$^{125}$I]FIAU.

In Silico Analysis of Bacterial TK

An in silico assessment of TK genes in all 53 pathogenic bacteria whose genomes have been sequenced and made publicly available was preformed. This assessment revealed that each of these bacterial species possessed TK genes. Moreover, the homology between these TK genes was striking, with a clear consensus within the kinase catalytic domain. Each of the 53 bacteria contained at least 25 residues that were identical to those of the consensus. In contrast, this consensus sequence was not found in mammalian TKs, presumably accounting for the differential capacities of the mammalian enzymes to phosphorylate substrates such as FIAU.

Imaging Infections Caused by Pathogenic Bacteria

In light of this high sequence conservation, it was expected that [$^{125}$I]FIAU could be used as a tracer for pathogenic bacteria in general. Four patient-derived strains identified in the Johns Hopkins Hospital Microbiological Laboratory were selected to test this expectation. The identities and clinical properties of the selected strains are listed in Table 1. Infectious foci due to *E. faecalis*, *S. aureus*, *S. epidermidis*, and *S. pneumoniae* could all be readily imaged with [$^{125}$I]FIAU. Robust signals could be observed as early as 4 h after administration of [$^{125}$I]FIAU. Time-course studies showed that [$^{125}$I] remained in the infected tissues for long time periods, presumably because [$^{125}$I]FIAU was incorporated into the DNA of the bacteria. In contrast to the maintenance of this bacterial signal, the background signal in noninfected tissues gradually decreased, presumably because of continuing metabolism and excretion of [$^{125}$I]FIAU. This resulted in very high signal-to-noise ratios by 48 h after administration of the tracer.

For quantitative distribution measurements, mouse thighs were infected with *S. aureus* 25923 and [$^{125}$I]FIAU was administered 6 h later. Tissues were harvested after another 24 h and radioactivity measured. The infected muscle contained much higher levels of [$^{125}$I]FIAU than the other tissues, with the ratio of radioactivity in infected thighs to uninfected (contralateral) thighs exceeding 14:1.

To determine the minimal number of bacteria that could be imaged with this approach, various numbers of *S. aureus* 25923 were injected into mouse thighs. One hour later, the thigh tissue was excised, homogenized, and spread on blood agar plates. The 1-h time point was chosen because this was the earliest time point at which injections of [$^{125}$I]FIAU consistently produced discernable scintigraphic images of infectious foci. As few as $2\times10^6$ colony-forming units per gram of muscle tissue produced discernable signals.

Imaging Intratumoral Infections

Imaging of infectious foci that were created by a process other than i.m. injection was performed. It has been shown that the spores of anaerobic bacteria, when systemically administered to mice, germinate only within tumor tissues. *C. novyi*-NT is a derivative of *C. novyi* that is devoid of its major systemic toxin gene and can therefore be safely delivered to animals. When injected i.v. into mice bearing tumors, <1% of the spores localize within tumors, the remainder being sequestered in the spleen and liver. The few spores localized within the tumor germinate rapidly, achieving a density of $\approx 10^8$ per gram of tissue by 24 h.

BALB/c mice bearing CT-26 mouse colon tumors were treated with a single i.v. injection of *C. novyi*-NT and [$^{125}$I]FIAU was administered 24 h later. Serial images showed that the tumors could be visualized as early as 16 h after injection of tracer, with maximum uptake observed 24-48 h after injection of [$^{125}$I]FIAU. No uptake was observed in tumors that had not been treated with *C. novyi*-NT. Similar results were obtained in nude mice harboring HCT116 and HT-29 colon cancer xenografts.

Because planar γ camera imaging is limited in its ability to reveal anatomical detail, SPECT/CT imaging was also performed. As observed in tumor-bearing rabbits treated with *C. novyi*-NT spores, areas of gas produced by the bacteria within CT-26 tumors could also be visualized upon CT, providing definitive evidence for infection. Coregistration of CT images with corresponding SPECT images demonstrated that bacterial germination and tracer uptake were limited to the tumor region. Untreated mice showed no signs of gas or tracer uptake within their tumors.

Imaging of Bacteriolytic Therapy

The following example sets forth the imaging of bacteria sequestered within the hypoxic core of a tumor.

A hallmark of almost all solid malignancies is the presence of significant hypoxia and necrosis. The engineered anaerobic bacterium *Clostridium novyi*-NT can selectively target and destroy experimental tumors. In order to follow *C. novyi*-NT in vivo after injection into mice iodine-125 labeled 2'-Fluoro 2'-deoxy 5-iodouracil-β-D-arabinofuranoside (1-125 FIAU) was used.

In vitro susceptibility tests were performed on *C. novyi*-NT using 96 well plates containing two-fold serial dilutions of FIAU (Moravek Biochemicals) in reinforced clostridial media (Difco). Approximately, $10^5$-$10^6$ bacteria were inoculated into each well and incubated at 37 C. overnight in an anaerobic chamber. *C. novyi*-NT growth was measured using an $OD_{600}$. In order to test the mechanism of action of FIAU on bacteria, the thymidine kinase (TK) gene in *E. coli* was knocked out. An in vitro FIAU susceptibility test comparing wild type *E. coli* with the mutant TK deficient *E. coli* was preformed. 96 well plates were used containing two-fold serial dilutions of FIAU in Lauria Broth. Approximately, $10^5$-$10^6$ bacteria were inoculated into each well and incubated at 37 C. overnight. Growth was measured using $OD_{600}$.

For in vivo studies, FIAU was labeled with 1-125. The optimal time course for imaging mice harboring HCTZ 16 colon cancer xenografts was determined empirically by varying the time of injection of FIAU in relation to *C. novyi*-NT. Biodistribution studies were performed in 12 athymic nu/nu mice harboring HCTZ 16 xenografts ~350-400 mm$^3$, six of which were injected with 300 million *C. novyi*-NT spores 24 hrs prior to 2 uCi of 1-125 FIAU. Eight hours after I-125 FIAU injection, all twelve mice were euthanized by cervical dislocation and the brain, lungs, heart, blood, small and large intestine, liver, kidneys, muscle and tumor were harvested and weighed. The activity in each tissue was measured using an automated gamma counter (LKB Wallace 1282 Compugamma CS Universal Gamma Counter). The percent-injected dose per gram of tissue (% ID/g) was calculated by comparison with samples of a standard dilution of the initial dose. At least three mice each harboring HCT116, HuCCTI biliary cancer xenograft, or CT26 mouse colon tumors were imaged using a dedicated Gamma Medica X-SPECT small animal SPECT camera after being injected with *Clostridium novyi*-NT spores and 150-200 uCi of I-125 FIAU.

*Clostridium novyi*-NT had a minimum inhibitory concentration 50 ($MIC_{50}$) of ~20 ug/ml of FIAU. Wild type *E. coli* had a $MIC_{50}$ of –10 ug/ml while the TK deficient *E. coli* were not inhibited at any concentration of FIAU tested. It was determined that *C. novyi*-NT germination could be optimally imaged under the following conditions: inject 300 million spores of *C. novyi*-NT and 24 hrs later inject 150-200 uCi of FIAU and image 8 hrs later.

The biodistribution studies revealed a 7:1 tumor:muscle ratio. All tumor types responsive to bacteriolytic therapy were able to be imaged using I-125 FIAU.

In vitro susceptibility tests suggested that *Clostridium novyi*-NT could potentially be imaged using I-125 FIAU. The putative mechanism off accumulation of FIAU within the bacteria is via phosphorylation of FIAU and its subsequent integration into bacterial DNA. Biodistribution and imaging data suggest that I-125 FIAU is a facile and robust method for imaging bacteriolytic therapy in mice.

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for monitoring the efficacy of treatment in a subject having a bacterial infection comprising: administering to the subject a first dose of a compound suitable for imaging which binds to a bacterial thymidine kinase present in the infecting organism; obtaining a first image of the subject to determine the presence and location of the compound; administering to the subject a second dose of a compound suitable for imaging which binds to a bacterial thymidine kinase present in the infecting organism at a time subsequent to the first administration; and obtaining a second image of the subject to determine the presence and location of the compound wherein the compound is a radiolabeled nucleoside; wherein a decrease in amount of compound localized to a particular location is indicative of effective therapy.

2. The method of claim 1, wherein the image of the subject is acquired by a method selected from the group consisting of

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgatgaaaag tagaacagtc g                                              21

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atcaagacgc agcaccatg                                                 19

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acatccacgg aagttttcag                                                20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccgaaggtta agctacctac                                                20
``` planar gamma imaging, single photon emission computed tomography (SPECT) and positron emission tomography (PET).

3. The method of claim 1, wherein the compound is a radiolabeled nucleoside analog.

4. The method of claim 3, wherein the nucleoside analog is labeled with radioactive fluorine or iodine.

5. The method of claim 4, wherein the compound is selected from the group consisting of 2'-fluoro-2'deoxy-1-beta-D-arabinofuranosyl-5-iodo-uracil ([1251]-FIAU), 2'-fluoro-2'deoxy-1-beta-D-arabinofuranosyl-5-iodo-uracil ([1241]-FIAU), 9-(4-18F-fluoro-3-[hydroxymethyl]butyl) guanine ([18F]-FHBG), (18)F-1-(2'-deoxy-2'-fluoro-beta-d-arabinofuranosyl)thymine ([18F]-FMAU), 18F-2'-fluoro-2'deoxy-1beta-D-arabinofuranosyl-5-ethyl-uracil ([18F]-FEAU) and 1-(2'-deoxy-2'-fluoro-beta-D-arabinofuranosyl)-5-[18F]iodouracil ([18F]-FIAU).

6. The method of claim 3, wherein the nucleoside analog emits gamma particles.

7. The method of claim 3, wherein the nucleoside analog is fluorescent.

8. The method of claim 1, wherein the bacterial infection is caused by bacteria from a genus selected from the group consisting of *Escherichia, Bacillus, Chromobacterium, Clostridium, Enteroccus, Haemophilus, Listeria, Mycoplasma, Pasteruella, Salmonella, Staphylococcus, Streptococcus, Streptomyces, Vibrio*, and *Yersinia*.

* * * * *